US009237751B2

(12) United States Patent
Reynolds

(10) Patent No.: US 9,237,751 B2
(45) Date of Patent: Jan. 19, 2016

(54) TOPICAL PARASITICIDE COMPOSITION

(75) Inventor: Louise Reynolds, County Down (GB)

(73) Assignee: NORBROOK LABORATORIES LIMITED, Newry (GB)

( * ) Notice: Subject to any disclaimer, the term of this patent is extended or adjusted under 35 U.S.C. 154(b) by 594 days.

(21) Appl. No.: 13/259,770

(22) PCT Filed: Mar. 29, 2010

(86) PCT No.: PCT/GB2010/000612
§ 371 (c)(1),
(2), (4) Date: Dec. 6, 2011

(87) PCT Pub. No.: WO2010/109214
PCT Pub. Date: Sep. 30, 2010

(65) Prior Publication Data
US 2012/0071484 A1 Mar. 22, 2012

(30) Foreign Application Priority Data
Mar. 27, 2009 (GB) .................................. 0905365.3

(51) Int. Cl.
A01N 43/58 (2006.01)
A01N 43/60 (2006.01)
A01N 43/40 (2006.01)
A01N 43/16 (2006.01)
A01N 37/34 (2006.01)
A01N 49/00 (2006.01)
A01N 43/90 (2006.01)
A01N 47/02 (2006.01)
A01N 51/00 (2006.01)
A61K 9/00 (2006.01)
A61K 9/08 (2006.01)
A61K 31/215 (2006.01)
A61K 31/365 (2006.01)
A61K 31/415 (2006.01)
A61K 31/4439 (2006.01)
A61K 31/495 (2006.01)

(52) U.S. Cl.
CPC .............. *A01N 49/00* (2013.01); *A01N 43/60* (2013.01); *A01N 43/90* (2013.01); *A01N 47/02* (2013.01); *A01N 51/00* (2013.01); *A61K 9/0014* (2013.01); *A61K 9/08* (2013.01); *A61K 31/215* (2013.01); *A61K 31/365* (2013.01); *A61K 31/415* (2013.01); *A61K 31/4439* (2013.01); *A61K 31/495* (2013.01)

(58) Field of Classification Search
CPC A61K 31/415; A61K 31/4439; A61K 31/495
USPC ................... 514/250, 347, 536, 460
See application file for complete search history.

(56) References Cited

U.S. PATENT DOCUMENTS

| 6,096,329 | A  | 8/2000  | Jeannin |
| 6,426,333 | B1 | 7/2002  | Huet et al. |
| 7,494,956 | B2 | 2/2009  | Gauvry et al. |
| 7,754,749 | B2 | 7/2010  | Anspaugh et al. |
| 2004/0063766 | A1 | 4/2004 | Bouvier et al. |
| 2004/0198676 | A1 | 10/2004 | Soll et al. |
| 2004/0254125 | A1 | 12/2004 | Saito et al. |
| 2004/0260097 | A1 | 12/2004 | Furch et al. |
| 2006/0014802 | A1 | 1/2006 | Billen et al. |
| 2006/0062817 | A1 | 3/2006 | Ahn et al. |
| 2007/0020304 | A1 | 1/2007 | Tamarkin et al. |
| 2008/0200540 | A1 | 8/2008 | Gibson et al. |

FOREIGN PATENT DOCUMENTS

| BR | PI 0403620-4 | 3/2008 |
| CA | 2399426 | * 2/2003 |
| EP | 1449435 | 8/2004 |
| EP | 1668984 | 6/2006 |
| GB | 2 457 734 | 8/2009 |
| JP | H11-508276 | 7/1999 |
| JP | 2003-081719 | 3/2003 |
| JP | 2003-201204 | 7/2003 |
| JP | 2007-510632 | 4/2007 |
| WO | WO 98/17277 | 4/1998 |
| WO | 0160409 | 8/2001 |
| WO | WO 02/094288 | 11/2002 |
| WO | 03042184 | 8/2003 |
| WO | 2004002537 | 1/2004 |
| WO | 2004024704 | 3/2004 |
| WO | 2006134466 | 12/2006 |
| WO | WO 2007/018659 | 2/2007 |
| WO | 2007082841 | 7/2007 |
| WO | 2008030385 | 3/2008 |
| WO | 2008096231 | 8/2008 |
| WO | WO 2008/136791 | 11/2008 |
| WO | 2009018198 | 2/2009 |

(Continued)

OTHER PUBLICATIONS de Souza et al., Transactions of the Royal Society of Tropical Medicine and Hygiene, vol. 76, No. 5, 1982, pp. 652-659.
Fipronil (354), The e-Pesticide Manual (Thrteenth Edition) Version 3.0, British Crop Protection Council, Jan. 1, 2003.
Lyons, et al., Veterinary Parasitology, 41 (1992) pp. 255-284.
Young, et al., Veterinary Parasitology 125 (2004) 397-407.
International Search Report and Written Opinion for PCT/GB2010/000612, mailed Jun. 12, 2011, 11 pgs.
Bianciardi et al., "Treatment of dog thelaziosis caused by *Thelazia callipaeda* (Spirurida, Thelaziidae) using a topical formulation of imidacloprid 10% and moxidectin 2.5%", Veterinary Parasitology 129, pp. 89-93 (2005).
Charles et al., "Evaluation of the efficacy of emodepside+praziquantel topical solution against cestode (*Dipylidium caninum, Taenia Taeniaeformis*, and *Echinococcus multicularis*) infections in cats", Parasitol Res. vol. 97, suppl. 1, pp. 33-40 (2005).

(Continued)

Primary Examiner — San-Ming Hui
(74) Attorney, Agent, or Firm — Porzio, Bromberg & Newman P.C.

(57) ABSTRACT

A topical parasiticide composition comprising: (i) a phenyl pyrazole insecticide; and/or a neonicotinoid; (ii) a macrocylic lactone and/or an aminoacetonitrile derivatives; (iii) an Insect Growth Regulator; and (iv) a 2-acyl-4-oxo-1,2,3,6,7,11b-4H-pyrazino[2,1a]isoquinoline derivative.

7 Claims, No Drawings

(56) References Cited

FOREIGN PATENT DOCUMENTS

| WO | WO 2009/018198 | 2/2009 |
|---|---|---|
| WO | 2009027506 | 3/2009 |
| WO | 2009033175 | 3/2009 |
| WO | WO 2009/027506 | 3/2009 |

OTHER PUBLICATIONS

Fourie et al., "The efficacy of an imidacloprid/moxidectin combination against naturally acquired *Sarcoptes scabiei* infestation on dogs", Australian Vet. J. vol. 84, No. 1 & 2, pp. 17-21 (2006).

Hubert et al., "Persistent efficacy of topical moxidectin against *Dictyocaulus viviparous* and *Ostertagia osterytagi*", Veterinary Parasitology 68, pp. 187-190 (1997).

Kaminsky et al., "Identification of the amino-acetonitrille derivative monepantel (AAD 1566 as a new anthelmintic drug development candidate", Parasitol. Res. 103 (4) pp. 931-939 (2008).

Notice of Opposition Australia Patents Act 1990, for Application AU 2010227340, 1 pg. Sep. 19, 2014.

Notice of Opposition to Grant of Patent (Sec. 21) in New Zealand for Application NZ 595934, 5 pgs. Jun. 28, 2014.

Patent Examination Report from Australian Government IP Australia, No. 1, for Appl. No. 2010227340, issued Nov. 7, 2013, 5 pgs.

Further Examination Report from Intellectual Property New Zealand for IP No. 595934, mailed Nov. 15, 2013, 2 pgs.

Translation of the Notice of Reasons for Rejection from JPO for appl. JP 2012-501386, mailed Mar. 11, 2014, 3 pgs.

European Office Action for Appl. No. EP 10711320, 3 pgs, Mar. 27, 2013.

Office Action from Eurasian Patent Office and its translation for appl. No. 201171173, mailed Apr. 9, 2014, 5 pgs.

Official Action with the partial translation from Mexican Office for Appl. No. MX/a2011/010102, 5 pgs. Aug. 13, 2014.

"Material Safety Data Sheet," Product Name: Advantage for Dogs and Cats; Bayer HealthCare, 2003 (revised 2008), 7 pages.

"Material Safety Data Sheet," Product Name: Advocate for Cats; Bayer HealthCare, 2003, 8 pages.

"Material Safety Data Sheet," Product name: Noromectin Pour-On for Cattle; Norbrook Laboratories Australia Pty Limited, 2004, 6 pages.

"Material Safety Data Sheet," Product Name: Profender for Cats; Bayer Australia Ltd, 2004 (revised 2012), 8 pages.

"Material Safety Data Sheet," Trade name: Fipronil 0.29% w/w Frontline® Spray Treatment; Merial, 2001, 7 pages.

"Material Safety Data Sheet," Trade name: Fipronil 9.7% w/w Frontline® Top Spot™; Merial, 2001, 7 pages.

"Material Safety Data Sheet," Trade name: Frontline® Plus for Dogs; Merial, 2001, 8 pages.

"Material Safety Data Sheet," Trade Name: Revolution; Pfizer Australia Pty Ltd, 2004, 5 pages.

"Safety Data Sheet," Product name: IVOMEC Pour-On for Cattle & Deer; Merial, 2007, 6 pages.

Bianciardi et al., "Treatment of dog thelaziosis caused by *Thelazia callipaeda* (*Spirurida, Thelaziidae*) using a topical formulation of imidacloprid 10% and moxidectin 2.5%," Veterinary Parasitology, 2005, 129, pp. 89-93.

Charles et al.," Evaluation of the efficacy of emodepside-i-praziquantel topical solution against cestode (*Dipylidium caninum*, *Taenia taeniaeformis*, and *Echinococcusmultilocularis*) infections in cats," Parasitol Res, 2005: 97(1), pp. S33-S40.

Definition of Derivative by Merriam Webster, [online], [retrieved on Dec. 19, 2014]. Retrieved from the Internet: <URL: http://www.merriam-webster.com/dictionary/derivative>.

Definition of Derivative by The Free Dictionary, [online], [retrieved on Dec. 19, 2014]. Retrieved from the Internet: <URL: http//www.thefreedictionary.com/derivative>.

Definition of Macrocyclic by The Free Dictionary, [online], [retrieved on Dec. 19, 2014]. Retrieved from the Internet: <URL: http://www.thefreedictionary.com/macrocyclic>.

Dictionary definition of Macrocyclic by Merriam Webster, [online], [retrieved on Dec. 19, 2014]. Retrieved from the Internet: <URL: http://www.merriamwebster.com/dictionary/macrocyclic>.

European Communication pursuant to Article 94(3) EPC, issued in related European Patent Application No. 10711920.8, dated Feb. 26, 2015, 5 pages.

Fourie et al., "The efficacy of an imidacloprid/moxidectin combination against naturally acquired *Sarcoptes scabiei* infestations on dogs," Australian Veterinary Journal, 2006: 84(1 & 2), pp. 17-21.

Hubert et al., "Persistent efficacy of topical moxidectin against *Dictyocaulus vivparus* and *Ostertagia ostertagi*," Vet. Parasitology, 1997: 68, pp. 187-190.

Liu et al., "Investigation of the Phase Diagrams of Chiral Praziquantel," Chirality, 2006: 18, pp. 259-264.

Lyons et al., " Critical and controlled tests of activity of moxidectin (CL 301,423 ) against natural infections of internal parasites of equids," Vet. Parasitology, 1992: 41, pp. 255-284.

Marked Up Notice of Opposition to Grant of Patent (Section 21), in related New Zealand Patent Application No. 595934, submitted by FB Rice, Aug. 28, 2014, 6 pages.

Notice of Opposition to Grant of Patent (Section 21), in related New Zealand Patent Application No. 595934, submitted by FB Rice, Aug. 28, 2014, 5 pages.

Notice of Opposition, in related Australian Patent Application No. 2010227340, submitted by FB Rice, Sep. 19, 2014, 1 page.

Seubert et al., "Synthesis and properties of praziquantel, a novel broad spectrum anthelmintic with excellent activity against Schistosomes and Cestodes," Experientia, 1977, pp. 1036-1037.

Statement of Case, in related New Zealand Patent Application No. 595934, submitted by FB Rice, Aug. 28, 2014, 31 pages.

The Merck Index: an Encyclopedia of Chemicals, Drugs, and Biologicals, "Praziquantel," 14th Edition. Merck Inc., Whitehouse Station, New Jersey, 2006, pp. 7717.

Third Party Observations under Article 115 EPC in related European Patent Application No. 10711920.8 submitted by Keltie LLP, Sep. 9, 2014, 10 pages.

United States Environmental Protection Agency, "New Pesticide Fact Sheet," Trade name Fipronil Technical; Chipco Choice Insecticide, 1996, 10 pages.

Young et al., "Efficacy of fipronil/(S)-methoprene combination spot-on for dogs against shed eggs, emerging and existing adult cat fleas (*Ctenocephalides felts*, Bouché)," Vet Parasitology, 2004: 125, pp. 397-407.

CAPlus Document No. 146:169274 which relates to Brazilian Patent Application BR PI 0403620. This document was added to the Chemical Abstracts Plus database on Feb. 8, 2007, 2 pages.

\* cited by examiner

TOPICAL PARASITICIDE COMPOSITION

The present invention relates to a parasiticide composition for topical application, and its use in a method of treating endo and ecto parasiticide infections of an animal, wherein the composition is applied topically to the skin of the animal.

Insect growth regulators (IGRs) like methoprene, hydroprene, kinoprene, fenoxycarb, pyriproxifen, cyromazine, dimilin and novaluron are a class of insecticides that inhibit chitin synthesis or the development of parasites from immature stages, like eggs and larvae, into the adults. Common ectoparasiticides which may be treated with insect growth regulators include fleas and ticks, for example the Siphonaptera order and *Ctencephalides Felis* and *Ctencephalides Canis*, human fleas like *Pulex Irritans*, rat fleas like *Xenopsylla Cheopis* and ticks like those of cattle (e.g. *Boophilus Microplus*) and of dog (*Rhipicephali Sanguineus*).

Topical parasiticide compositions are known, and may be in the form of spot-on products. Typically, only a few milliliters of such spot-on products containing an ectoparasiticide are administered onto a localised area on an animal's back. 24 hours after application, the complete skin surface of the animal is protected by the ectoparsiticide. It is believed that upon application, the insecticide is adsorbed onto the skin surface and solubilised in the skin sebum from where it spreads along the surface by diffusion. Reservoirs of the insecticide are believed to form in the sebaceous glands thereby providing a supply of the drug over a long period of time, e.g. from 6 to 8 weeks of protection.

Examples of formulations containing methoprene which are effective against ticks include U.S. Pat. No. 5,194,264 which describes an aqueous/polar solvent methoprene composition. U.S. Pat. No. 6,492,419 discloses a composition with an Insect Growth Regulator (IGR) in a vehicle comprising a suspending agent, an anionic surfactant, a non-ionic surfactant or mixtures thereof, and an aqueous carrier.

The use of Fipronil in topical parasiticide compositions is known for the eradication or reduction of ectoparasites from the skin of an animal.

A methoprene fipronil combination spot-on product exists (Frontline™ Plus). In this product the active agents are solubilised in ethanol and a number of excipients including povidone, diethyleneglycolmonoethylether and antioxidants are required for stability and to inhibit crytalisation of the actives, especially on the skin surface of the animal.

It is an object of the present invention to provide a stable topical composition for application to humans or animals which provides efficacious levels of insecticide activity to the treated human or animal for a number of days or weeks. The composition is for use in treating endo and ecto parasiticide infection of animals by the topical application of the composition.

In the first aspect of the present invention there is provided a topical parasiticide composition comprising:
  (i) a phenyl pyrazole insecticide; and/or a neonicotinoid;
  (ii) a macrocylic lactone and/or an aminoacetonitrile derivative;
  (iii) an Insect Growth Regulator; and
  (iv) an 2-acyl-4-oxo-1,2,3,6,7,11b-4H-pyrazino[2,1a]isoquinoline derivative.

In the second aspect of the present invention there is provided a composition as described herein for use in a method of treatment of the human or animal body by therapy.

In the third aspect of the present invention there is provided a composition as described herein for use in a method of treating endo and ecto parasiticide infections of an animal, wherein the composition is applied topically to the skin of the animal.

In the fourth aspect of the present invention there is provided the use of a composition as defined in herein in a method of treatment of endo and ecto parasiticide infections of an animal, wherein the composition is applied topically to the skin of the animal.

Each aspect as defined herein may be combined with any other aspect or aspects unless clearly indicated to the contrary. In particular any feature indicated as being preferred or advantageous may be combined with any other feature or features indicated as being preferred or advantageous.

The mixture of actives chosen in the present combination advantageously allows both endo and ecto parasitic infections to be treated by the topical application of just one composition to the infected human or animal.

Preferably the phenyl pyrazole insecticide has the formula (I)

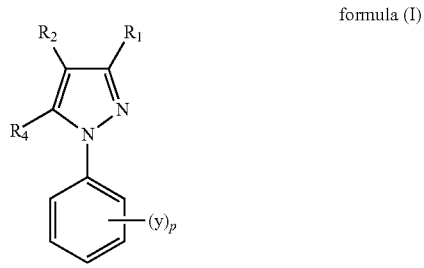

formula (I)

in which:
$R_1$ is a halogen atom, CN or methyl;
$R_2$ is $S(O)_n R_3$ or 4,5-dicyanoimidazol-2-yl or haloalkyl;
$R_3$ is alkyl or haloalkyl, for example lower haloalkyl;
$R_4$ represents a hydrogen or halogen atom; or a radical $NR_5R_6$, $S(O)_m R_7$, $C(O)R_7$ or $C(O)OR_7$, alkyl, haloalkyl or $OR_8$ or a radical —N—$C(R_9)(R_{10})$;
$R_5$ and $R_6$ independently represent a hydrogen atom or an alkyl, haloalkyl, C(O)alkyl, $S(O)_r CF_3$, acyl or alkoxycarbonyl radical; or $R_5$ and $R_6$ may together form a divalent alkylene radical which may be interrupted by one or two divalent hetero atoms such as oxygen or sulphur;
$R_7$ represents an alkyl or haloalkyl radical;
$R_8$ represents an alkyl or haloalkyl radical or a hydrogen atom;
$R_9$ represents an alkyl radical or a hydrogen atom;
$R_{10}$ represents a phenyl or heteroaryl group optionally substituted with one or more halogen atoms or groups such as OH, —O-alkyl, —S-alkyl, cyano or alkyl;
Y represents a halogen atom or a haloalkyl or haloalkoxy radical, for example a lower haloalkoxy radical, or an $SF_5$ radical, with the possibility that:
Y is CN or $NO_2$ in positions 2 and 6 (with reference to the carbon of the phenyl ring which is attached to the pyrazole ring and designated 1);
the carbon in position 2 of the phenyl ring is replaced by a trivalent nitrogen atom;
Y is $S(O)_q CF_3$ in position 4 on the phenyl ring, but preferably haloalkyl, haloalkoxy or $SF_5$;
m, n, q and r represent, independently of each other, an integer equal to 0, 1 or 2;
p is an integer equal to 1, 2, 3, 4 or 5, preferably equal to 1, 2 or 3, in particular 3;

with the proviso that when $R_1$ is methyl, then either $R_3$ is haloalkyl, $R_4$ is $NH_2$, p is 2, Y in position 6 is Cl, Y in position 4 is $CF_3$ and the carbon in position 2 of the phenyl is replaced by N; or $R_2$ is 4,5-dicyanoimidazol-2-yl, $R_4$ is Cl, p is 3, Y in position 6 is Cl, Y in position 4 is $CF_3$ and the carbon in position 2 of the phenyl is replaced by =C—Cl.

As used herein the term lower haloalkoxy radicals preferably refers to haloalkoxy radicals having $C_1$-$C_4$ carbon atoms.

Preferably the insecticide of formula (I) is 1-[2,6-$Cl_2$ 4-$CF_3$ phenyl]3-CN 4-[SO—$CF_3$]5—$NH_2$ pyrazole, (also known as 5-amino-1-(2,6-dichloro-4-trifluoromethylphenyl)-3-cyano-4-trifluoromethyl sulphinyl pyrazole) whose common name is Fipronil.

The compounds of formula (I) may be prepared, for example, according to one of the processes described in, for example, patent application WO-A-87/3781.

Mixtures of two or more phenyl pyrazole insecticides may be used in the present invention.

Preferably the composition comprises from 0.01 to 30% (w/v) phenyl pyrazole insecticide based on the total volume of the composition. More preferably the composition comprises from 0.01 to 20% (w/v) phenyl pyrazole insecticide based on the total volume of the composition. More preferably still the composition comprises from 0.1 to 10% (w/v), or from 0.5 to 5% (w/v), phenyl pyrazole insecticide based on the total volume of the composition.

In one embodiment of the present invention the composition comprises a neonicotinoid. Examples of suitable neonicotinoids are: Imidacloprid, Nithiazine, Nitenpyram, Acetamiprid, Thiamethoxam, Clothianidin and Dinotefuran. Mixtures of two or more neonicotinoids may be used in the composition of the present invention. Preferably the neonicotinoid is Imidacloprid.

Preferably the composition comprises from 0.01 to 30% (w/v) Neonicotinoid based on the total volume of the composition. More preferably the composition comprises from 0.01 to 20% (w/v) Neonicotinoid based on the total volume of the composition. More preferably still the composition comprises from 0.1 to 10% (w/v), or from 0.5 to 5% (w/v), Neonicotinoid based on the total volume of the composition.

Preferably the composition comprises from 0.01 to 30% (w/v) Imidacloprid based on the total volume of the composition. More preferably the composition comprises from 0.01 to 20% (w/v) Imidacloprid based on the total volume of the composition. More preferably still the composition comprises from 0.1 to 10% (w/v), or from 0.5 to 5% (w/v), Imidacloprid based on the total volume of the composition.

The composition of the present invention comprises one or more macrocylic lactones and/or one or more aminoacetonitrile derivatives. The one or more macrocylic lactones and/or aminoacetonitrile derivatives may be selected to treat endo and/or ecto parasites. Preferably the one or more macrocylic lactones and/or aminoacetonitrile derivatives have anthelmintic properties. They may also treat internal worm infections. The aminoacetonitrile derivative may be, for example, monepantel. The macrocylic lactone may comprise a milbemycin, such as milbemycine oxime. Examples of Milbemycine oximes include, but are not limited to, avermectins, ivermectin, selamectin, moxidectin, abamectin and doramectin. The macrocylic lactone is preferably Moxidectin. Moxidectin is the common name for (6R,23E,25S)-5-O-demethyl-28-deoxy-25-[(1E)-1,3-dimethyl-1-butenyl]-6,28-epoxy-23-(methoxyimino)milbemycin B. Pharmaceutically or veterinarily acceptable derivatives or prodrugs of Moxidectin may also be used. Moxidectin is well known, for example, for the treatment of heart worms in dogs.

Preferably the composition comprises from 0.01 to 30% (w/v) of one or more macrocylic lactones and/or one or more aminoacetonitrile derivatives based on the total volume of the composition. More preferably the composition comprises from 0.01 to 20% (w/v) one or more macrocylic lactones and/or aminoacetonitrile derivatives based on the total volume of the composition. More preferably still the composition comprises from 0.1 to 10% (w/v), or from 0.5 to 5% (w/v), one or more macrocylic lactones and/or aminoacetonitrile derivatives based on the total volume of the composition.

In a preferred embodiment the composition comprises from 0.01 to 30% (w/v) Moxidectin based on the total volume of the composition. More preferably the composition comprises from 0.01 to 20% (w/v) Moxidectin based on the total volume of the composition. More preferably still the composition comprises from 0.1 to 10% (w/v), or from 0.5 to 5% (w/v), Moxidectin based on the total volume of the composition.

Preferably, the Insect Growth Regulator is selected from methoprene, s-methoprene, hydroprene, s-hydroprene, kinoprene, s-kinoprene, fenoxycarb, pyriproxifen, cyromazine, dimilin, novaluron, pharmaceutically or veterinarily acceptable derivatives or prodrugs thereof and mixtures of two or more thereof. Most preferably the Insect Growth Regulator is s-methoprene or methoprene, pharmaceutically or veterinarily acceptable derivatives or prodrugs thereof and mixtures of two or more thereof.

Preferably the composition comprises from 0.01 to 30% (w/v) Insect Growth Regulator based on the total volume of the composition. More preferably the composition comprises from 0.01 to 20% (w/v) Insect Growth Regulator based on the total volume of the composition. More preferably still the composition comprises from 0.1 to 10% (w/v), or from 0.5 to 5% (w/v), Insect Growth Regulator based on the total volume of the composition.

In a preferred embodiment the composition comprises from 0.01 to 30% (w/v) s-methoprene based on the total volume of the composition. More preferably the composition comprises from 0.01 to 20% (w/v) s-methoprene based on the total volume of the composition. More preferably still the composition comprises from 0.1 to 10% (w/v), or from 0.5 to 5% (w/v), s-methoprene based on the total volume of the composition.

One or more 2-acyl-4-oxo-1,2,3,6,7,11b-4H-pyrazino[2,1a]isoquinoline derivatives are present in the composition of the present invention. Preferably, the 2-acyl-4-oxo-1,2,3,6,7,11b-4H-pyrazino[2,1a]isoquinoline derivatives is Praziquantel. Praziquantel is the common name for 2-(Cyclohexylcarbonyl)-1,2,3,6,7,11b-hexahydro-4H-pyrazino (2,1-alpha) isoquinolin-4-one. Pharmaceutically or veterinarily acceptable derivatives or prodrugs of Praziquantel is known for treating of all forms of schistosomiasis, like fluke and the Common Tapeworm of dogs & cats (Dipylidium caninum).

Preferably the composition comprises from 0.01 to 30% (w/v) one or more 2-acyl-4-oxo-1,2,3,6,7,11b-4H-pyrazino[2,1a]isoquinoline derivatives based on the total volume of the composition. More preferably the composition comprises from 0.01 to 20% (w/v) one or more 2-acyl-4-oxo-1,2,3,6,7,11b-4H-pyrazino[2,1a]isoquinoline derivatives based on the total volume of the composition. More preferably still the composition comprises from 0.1 to 10% (w/v) one or more 2-acyl-4-oxo-1,2,3,6,7,11b-4H-pyrazino[2,1a]isoquinoline derivatives based on the total volume of the composition.

In a preferred embodiment the composition comprises comprises from 0.01 to 30% (w/v) Praziquantel based on the total volume of the composition. More preferably the composition comprises from 0.01 to 20% (w/v) Praziquantel based on the total volume of the composition. More preferably still the composition comprises from 0.1 to 10% (w/v) Praziquantel based on the total volume of the composition.

Preferably the composition comprises Fipronil, Moxidectin, S-methoprene and Praziquantel.

Preferably the composition comprises Imidacloprid, Moxidectin, S-methoprene and Praziquantel.

Preferably the composition of the present invention comprises one or more solvents. The solvent may be selected from at least one pyrrolidone, cyclic carbonate, glycol ether, alcohol, DMSO, and mixtures of two or more thereof. Preferably the solvent is selected from at least one pyrrolidone, cyclic carbonate, DMSO, and mixtures of two or more thereof.

Any suitable pyrrolidone may be used, for example the pyrrolidone may be selected from N-methylpyrrolidone, 2-pyrrolidone and mixtures thereof.

The solvent may comprise 100% of one or more pyrrolidone(s). Alternatively, the solvent may comprise one or more pyrrolidones and DMSO in a ratio of from 9:1 to 1:9. The solvent may comprise one or more pyrrolidones and one or more cyclic carbonates in a ratio of from 9:1 to 1:9. The solvent may comprise N-methylpyrrolidone and DMSO, preferably in a ratio of from 9:1 to 1:9. It may comprise 2-pyrrolidone and DMSO, preferably in a ratio of from 9:1 to 1:9. The solvent may comprise N-methylpyrrolidone and propylene carbonate, preferably in a ratio of from 9:1 to 1:9. The solvent may comprise 2-pyrrolidone and propylene carbonate, preferably in a ratio of from 9:1 to 1:9.

The cyclic carbonate may be selected from ethylene carbonate, propylene carbonate, butylenes carbonate, glycerine carbonate and mixtures of two or more thereof. Preferably the cyclic carbonate is propylene carbonate.

Preferably the composition of the present invention comprises at least 60% (w/v) of solvent based on the total volume of the composition. More preferably it comprises at least 70% (w/v), at least 80% (w/v), or at least 90% (w/v) of solvent based on the total volume of the composition.

Other suitable solvents may be present in the topical composition. Suitable other solvents include, but are not limited to acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, diethylene glycol monoethyl ether, ethylene glycol, diethyl phthalate, and mixtures of two or more thereof. The preferred additional solvents are the glycol ethers. The glycol ether may be selected from ethylene glycol monoethyl ether, diethylene glycol monoethyl ether, ethylene glycol monomethyl ether, diethylene glycol monomethyl ether, propylene glycol monoethyl ether, dipropylene glycol monoethyl ether, propylene glycol monomethyl ether, dipropylene glycol monomethyl ether and mixtures of two or more thereof.

In one embodiment of the present invention the composition may be free of crystallisation inhibitor. This has the advantage that the composition may be made more cheaply and efficiency, whilst still being effective. Advantageously, the composition of the present invention comprises less than 25% (w/v) of crystallisation inhibitor, more preferably less than 10% (w/v), more preferably still less than 1% (w/v).

As used herein the term "crystallisation inhibitor" may be used to mean an agent or substance which inhibits crystal formation of the actives in the solvent when 10 ml of the composition is stored at 20° C. for 24 hours.

In an alternative embodiment, the composition of the present invention may comprise at least one crystallisation inhibitor. Suitable crystallisation inhibitors are known in the art and include, but are not limited to polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose; acrylic derivatives such as methacrylates and the like, anionic surfactants such as alkaline stearates, in particular sodium, potassium or ammonium stearate; calcium stearate, triethanolamine stearate; sodium abietate; alkyl sulphates, in particular sodium lauryl sulphate and sodium cetyl sulphate; sodium dodecylbenzenesulphonate, sodium dioctylsulphosuccinate; fatty acids, in particular those derived from coconut oil, cationic surfactants such as water-soluble quaternary ammonium salts of formula $N^+R'R''R'''R''''Y^-$ in which the radicals R are hydrocarbon radicals, optionally hydroxylated, and $Y^-$ is an anion of a strong acid such as halide, sulphate and sulphonate anions; cetyltrimethylammonium bromide is among the cationic surfactants which can be used, amine salts of formula $NR'R''R'''$ in which the radicals R are optionally hydroxylated hydrocarbon radicals; octadecylamine hydrochloride is among the cationic surfactants which can be used, nonionic surfactants such as optionally polyoxyethylenated sorbitan esters, in particular polysorbate 80, polyoxyethylenated alkyl ethers; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, amphoteric surfactants such as lauryl-substituted betaine compounds, or preferably a mixture of at least two of these crystallization inhibitors.

The composition may comprise at least one adjuvant selected from anti-oxidants and other actives.

Suitable antioxidants include, but are not limited to butylated hydroxyanisole (BHA), butylated hydroxytoluene, ascorbic acid, sodium metabisulphite, propyl gallate, sodium thiosulphate, and mixtures of two or more thereof. Preferred antioxidants are butylated hydroxyanisole (BHA) and butylated hydroxytoluene. Addition of antioxidants may be advantageous in extending the shelf-life of the compositions.

Preferably in the composition anti-oxidants are present in a concentration of from 0.005 to 1% (w/v) based on the total composition, more preferably from 0.01 to 0.05% (w/v).

The other-actives may be selected from one or more of spinosads, non-steroidal anti-inflammatory drugs (NSAIDs), steroidal anti-inflammatory drugs, chitin synthesis inhibitors and RNA inhibitors.

Suitable non-steriodal anti-inflammatory drugs (NSAID) include, but are not limited to, ibuprofen, carprofen, meloxicam and acetaminophen.

Suitable steroidal anti-inflammatory drugs include, but are not limited to, codeine, cortisone and hydro-cortisone.

Examples of chitin synthesis inhibitors include, but are not limited to, triflumuron, lufenuron, chlorofluazuron and fluazuron.

Suitable amounts of the other-actives will depend on the actives used in question. Typically the other-actives may be present in a concentration of from 0.1 to 30% (w/v) based on the total volume of the composition, preferably from 5 to 20% (w/v).

Other actives include agents which with the composition of the present invention may be sprayed, squirted, or rubbed on to the skin. These include, for example, conventional propellant gases required for spray cans, such as propane, butane, dimethyl ether, $CO_2$, or halogenated lower alkyl gases (for example, halogenated $C_1$-$C_4$ alkyls), and mixtures of two or more thereof.

The compositions according to the invention are usually prepared by simply mixing the constituents as defined above. Advantageously, to begin with, the active agents (i) to (iv) are mixed into the main solvent, and the other ingredients or adjuvants are subsequently added.

The compositions according to the invention are typically intended for pets, in particular cats and dogs, and are generally applied by deposition on the skin ("spot on" or "pour on" application). This is generally a localized application to a region with a surface area of less than 10 $cm^2$, typically between 5 and 10 $cm^2$. The composition may, for example, by applied at one, two or more points and is preferably localized between the animal's shoulders. After deposition, the composition diffuses, in particular over the animal's entire body, and then dries, without crystallizing or changing the appearance (in particular absence of any whitish deposit or of any dusty appearance) or the feel of the coat. The composition of the present invention may be a spot-on or a spray-on formulation.

The compositions according to the present invention are particularly advantageous on the grounds of their efficacy, their speed of action and the pleasant appearance of the animal's hair after application and drying.

It is preferable that the composition of the present invention is administered every 4 weeks or even more preferably every 8 or 12 weeks on small animals, such as cats and dogs.

The volume applied to a dog is typically from 0.25 to 3 ml and to a cat is typically from 0.25 to 1 ml.

The composition of the present invention may be used to treat insect infestation on humans, large and small animals, birds and reptiles. The larger the animal to be treated, the larger the dose volume of the composition to be applied. The composition of the present invention is especially suitable for administration to dogs and cats.

The composition of the present invention may be used to improve the appearance and texture of the animals' coat by elimination of the insects therefrom and any consequential irritation caused, however slight, to the infected animal. One object of the present invention is to provide a non-therapeutic method of cleaning animal hairs and skin by the reduction or elimination of parasites which are present in the animal hair or skin. The treated animals have hair that has a more pleasant look and feel.

Additionally, the compositions of the current invention may be used prophylactically in order to prevent infestation by insects like fleas or even ticks. The compositions may be used such that the treated animal are used as vectors in order to irradiate or reduce insects (for example ticks) from the animals environment, e.g. like bedding, carpet, floors and walls.

In one embodiment, the present invention provides a therapeutic treatment, and the composition may be used in a method of treatment for the eradication or reduction of ecto parasites from the skin of an animal, wherein the composition is applied topically to the skin of the animal. The process described herein may be used to control ectoparasites, and in particular ticks.

In further embodiment the present invention provides a method for the reduction or eradication of ecto and/or endo parasites from an animal, the method comprising applying the topical as defined herein to the skin of an animal. Preferably the topical composition is in the form of a spot-on composition. Preferably the composition is applied between the shoulders of the animal. Preferably the animal is a dog or a cat.

Preferably, the composition comprises fipronil. Preferably the composition is applied in unit dosage form.

In one aspect of the present invention there is provided the use of a composition as described herein in the manufacture of a medicament for the prevention or reduction of ecto and/or endo parasites from an animal.

The compositions of the present invention are for use in treating endo and ecto parasiticide infections in animals by the topical application of the composition.

The phenyl pyrazole insecticides and/or neonicotinoids may treat most ectoparasiticide insects especially members of the order of Diptera like flies and fleas.

Insect Growth regulators prevent maturation of the ectoparasiticide eggs.

The macrocyclic lactones and milbemycins preferably treat endo as well as ecto parasiticides, but mainly they are used to treat internal worm infections. Moxidectin is preferably used to treat heart worm in dogs.

Praziquantel may be used to treat endo parasites like liver fluke and common tape worm in dogs and cats.

The present invention will be further illustrated with reference to the following non-limiting Examples. q.s. as used herein means quantity sufficient.

EXAMPLE 1-5

The following 5 ml preparations were prepared from:

| | |
|---|---|
| Imidacloprid | 400 mg |
| Moxidectin | 100 mg |
| S-methoprene | 240 mg |
| Praziquantel | 320 mg | q.s. 100% of solvent.

The following solvent systems were used:
Example 1 solvent: N-methyl pyrrolidone
Example 2 solvent: 2-pyrrolidone
Example 3 solvent: 1:1 N-methyl pyrrolidone: 2-pyrrolidone
Example 4 solvent: propylene carbonate
Example 5 solvent: DMSO

The invention claimed is:

1. A spot-on or pour-on composition for the treatment of endo- and ecto-parasites comprising:
   (i) from 0.1 to 10% (w/v) of Fipronil based on the total volume of the composition;
   (ii) from 0.1 to 10% (w/v) of a macrocyclic lactone based on the total volume of the composition;
   (iii) from 0.1 to 10% (w/v) of Methoprene based on the total volume of the composition;
   (iv) from 0.1 to 10% (w/v) of Praziquantel based on the total volume of the composition; and
   wherein the composition comprises an alcohol solvent.

2. The composition of claim 1 wherein the macrocyclic lactone is Moxidectin.

3. The composition of claim 1 comprising Fipronil, Moxidectin, S-methoprene and Praziquantel.

4. The composition according to claim 1 wherein the composition comprises at least 60% (w/v) of solvent based on the total volume of the composition.

5. A composition according to claim 1 comprising at least one adjuvant selected from anti-oxidants, crystallization inhibitor and other actives.

6. A composition according to claim 1 which is in the form of a spray-on formulation.

7. A method of treating a human or animal infected with endo and ecto parasiticides, the method comprising applying to the skin of the infected human or animal the composition as defined in claim 1.

\* \* \* \* \*